United States Patent [19]

Hanosh

[11] Patent Number: 5,611,688
[45] Date of Patent: *Mar. 18, 1997

[54] EXPANDING DENTAL IMPLANT AND METHOD FOR ITS USE

[76] Inventor: Frederick N. Hanosh, 6756 Rancho Oaks Rd., Magalia, Calif. 94954

[*] Notice: The term of this patent shall not extend beyond the expiration date of Pat. No. 5,489,210.

[21] Appl. No.: 439,367

[22] Filed: May 11, 1995

Related U.S. Application Data

[63] Continuation-in-part of Ser. No. 242,258, May 13, 1994, Pat. No. 5,489,210.

[51] Int. Cl.$^6$ .................................................... A61C 8/00
[52] U.S. Cl. ............................................. 433/174; 433/173
[58] Field of Search .................................... 433/172, 173, 433/174, 175, 176; 606/72, 73

[56] References Cited

U.S. PATENT DOCUMENTS

| | | | |
|---|---|---|---|
| 2,721,387 | 10/1955 | Ashuckian | 32/10 |
| 2,857,670 | 4/1956 | Kiernan, Jr. | 32/10 |
| 3,579,831 | 5/1971 | Stevens | 32/10 |
| 3,708,883 | 1/1973 | Flander | 32/10 |
| 4,011,602 | 3/1977 | Rybicki et al. | 3/1.9 |
| 4,431,416 | 2/1984 | Niznick | 433/174 |
| 4,484,570 | 11/1984 | Sutter et al. | 128/92 |
| 4,523,587 | 6/1985 | Frey | 128/92 |
| 4,588,381 | 5/1986 | Caracciolo | 433/173 |
| 5,004,421 | 4/1991 | Lazarof | 433/173 |
| 5,013,242 | 5/1991 | Prezmecky | 433/174 |
| 5,087,199 | 2/1992 | Lazarof | 433/173 |
| 5,209,753 | 5/1993 | Biedermann et al. | 606/72 |

FOREIGN PATENT DOCUMENTS 1075793  2/1960  Germany.

Primary Examiner—Nicholas D. Lucchesi
Attorney, Agent, or Firm—Donald E. Schreiber

[57] ABSTRACT

The technical field of the invention generally concerns an expandable dental implant for receiving and supporting a dental prosthesis. The expandable dental implant, securable within a bore formed into bone of a patient's jaw, includes an elongated, hollow, tubular barrel having both an attachment end and an insertion end. The barrel has both a threaded interior surface for screwing the implant into the bore, and a threaded exterior surface for receiving a threaded expander screw. The barrel is pierced about its insertion end by a plurality of radial slits spaced circumferentially around the barrel. The interior surface of the barrel at the insertion end is formed with a smaller diameter than the diameter of the interior surface of the barrel at the attachment end. The expander screw and the interior surface of the barrel are shaped so advancement of the expander screw along the barrel toward the insertion end causes an end surface of the expander screw to collide with the interior surface of the barrel, and to expand the insertion end outward into the surrounding bone.

15 Claims, 2 Drawing Sheets

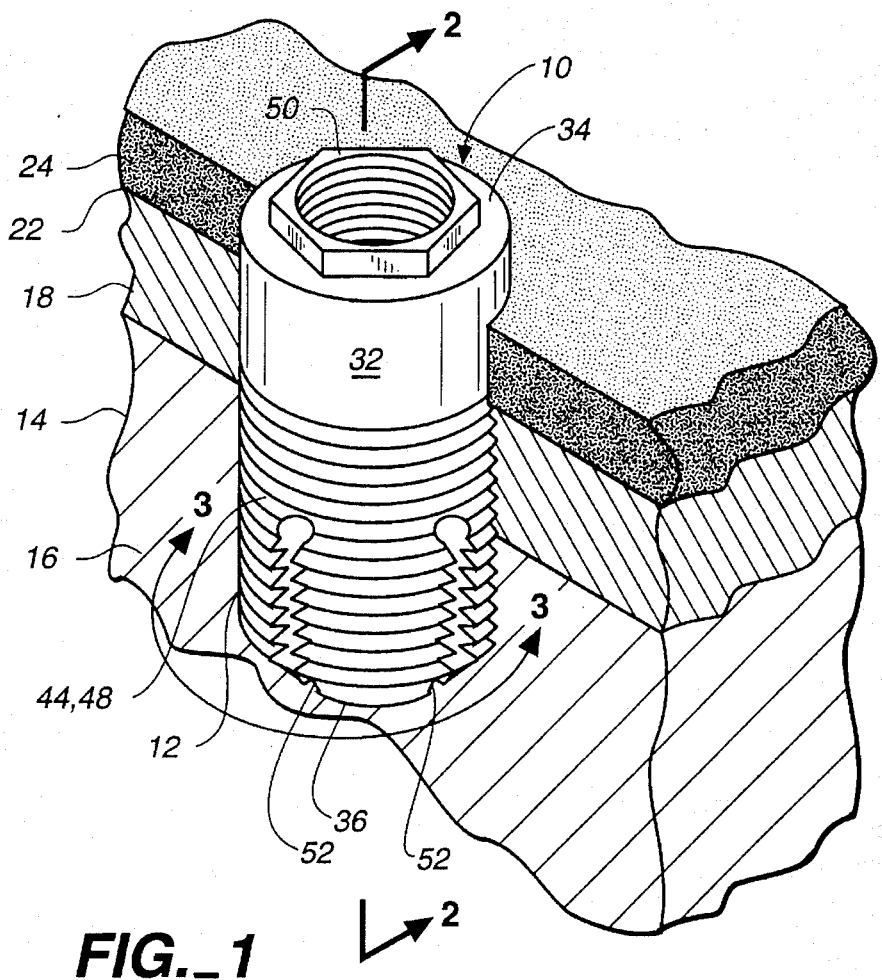
FIG._1
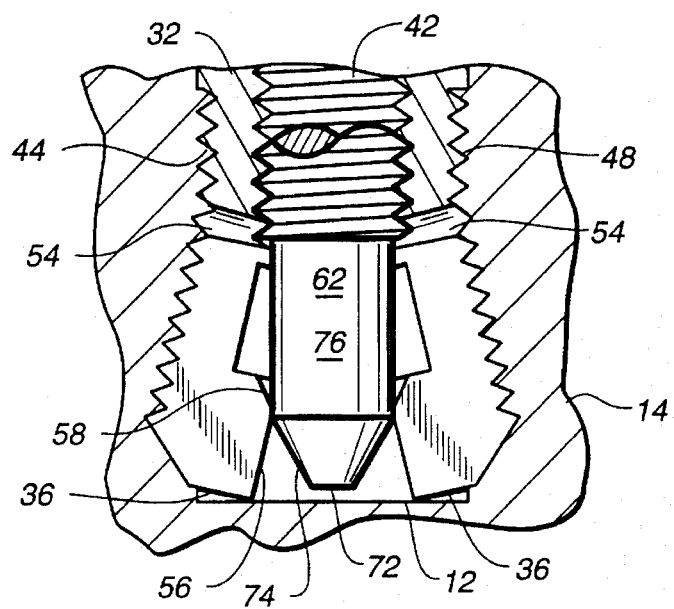
FIG._3

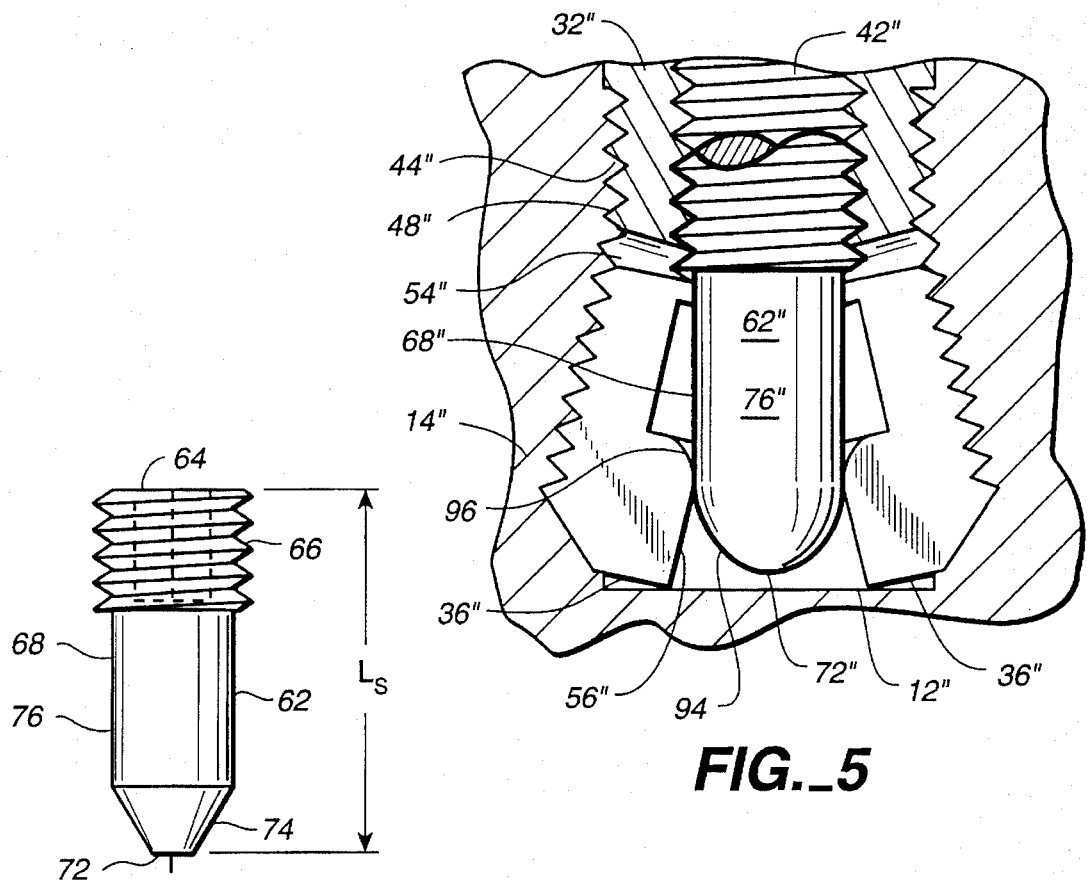
FIG._5
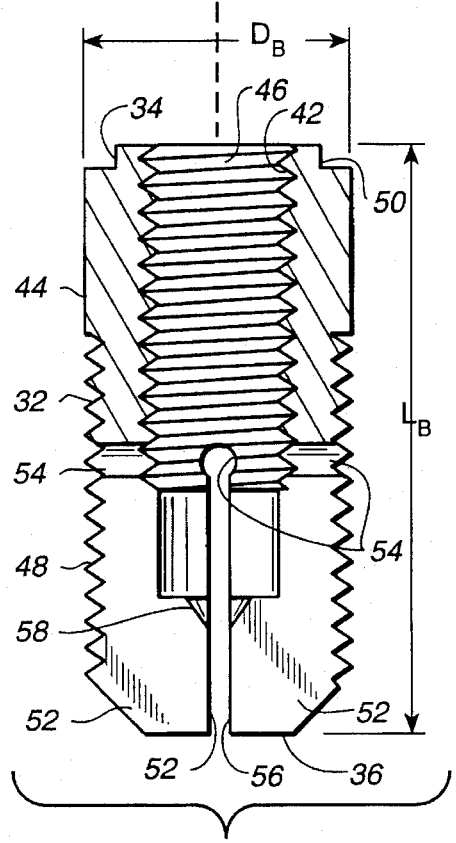
FIG._2
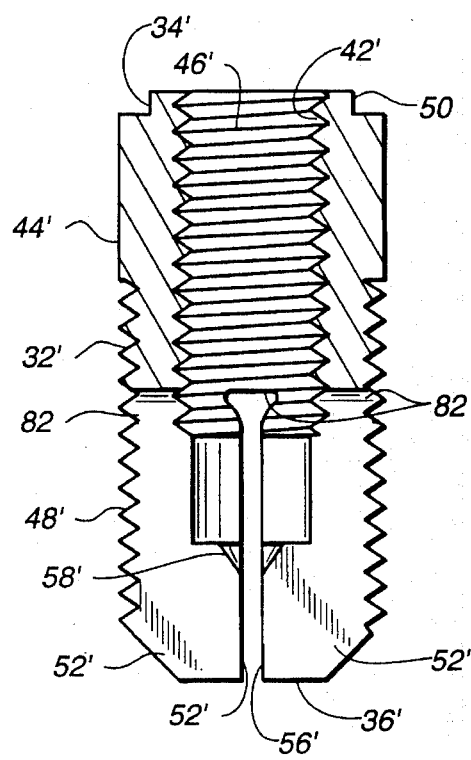
FIG._4

EXPANDING DENTAL IMPLANT AND METHOD FOR ITS USE

CROSS-REFERENCE TO RELATED APPLICATION

This application is a continuation-in-part of application Ser. No. 08/242,258, filed May 13, 1994 now U.S. Pat. No. 5,489,210.

BACKGROUND OF THE INVENTION

1. Field of the Invention

The present invention relates generally to the technical field of dentistry and, more particularly, to a dental implant installed into a patient's jaw to support a dental prosthesis.

2. Description of the Prior Art

U.S. Pat. No. 2,721,387 which issued Jul. 13, 1953, to Edward S. Ashuckian ("the Ashuckian Patent") discloses various different structures that are adapted for implantation into a socket from which a tooth has just been extracted. The various implants disclosed in the patent are shaped to fill the cavity previously occupied by the root of the extracted tooth. The Ashuckian Patent cautions that an X-ray must be taken prior to extracting the natural tooth to determine the shape and location of the root system so that an implant properly shaped for the socket is at hand when the tooth is extracted. The Ashuckian Patent states that its various structures all lend themselves to ready, rapid, and firm integration with the surrounding structure. In particular, FIG. 9 of the Ashuckian Patent discloses an implant in which, after its insertion into the socket of the extracted tooth, rotation of a threaded screw draws a nut toward the middle of the implant thereby spreading apart two legs then located within the socket. Nevertheless, the Ashuckian Patent acknowledges that a crown may not be placed on the implant until the healing process, which integrates the implant into the jaw, is well advanced or completed. The Ashuckian Patent cautions that if the implant is not held firmly in place within the jaw, it will move and work in the socket, and enlarge and irritate the surrounding structure.

U.S. Pat. No. 3,579,831 which issued May 25, 1971, to Irving J. Stevens ("the Stevens Patent") discloses an elongated dental implant which threads into a cylindrically-shaped bore formed into a jawbone. One end of the implant includes two self-tapping threaded surfaces that are divided along their length by an elongated notch or slit. The slit permits the threaded ends of the implant to flex resiliently toward and away from each other during insertion into the bore thereby enhancing the implant's self-threading action. The other end of the implant is formed to provide a fastening means to which a crown may be secured, and to concurrently provide an attachment location for a tool used in threading the implant into the bore. The implant disclosed in the Stevens Patent further includes at least one stabilizing pin that passes obliquely through the implant into the jawbone which prevents the implant's rotation. The Stevens Patent discloses that this implant, including its pin, addresses a problem of implant stability, and resists loosening of the implant due to stresses and vibrations.

U.S. Pat. No. 3,708,883 which issued Jan. 9, 1973, on an application filed by Stanley Flander ("the Flander Patent") discloses an implant which includes an elongated tubular body having a pair of extensions formed with inner surfaces which diverge away from each other. A spreader screw, having a T-shaped head which engages the diverging inner surfaces of the tubular body, extends along the body's entire length to project out the end of the body furthest from the diverging extensions. After the body's extensions and the T-shaped spreader screw have been inserted into a bore formed into the jawbone of a patient, rotating a nut threaded onto the end of the spreader screw that projects out of the bore beyond the tubular body draws the T-shaped head of the spreader screw along the length of the body thereby forcing the extensions to spread apart within the bore formed in the jawbone.

U.S. Pat. No. 4,431,416 which issued Feb. 14, 1984, on an application filed by Gerald A. Niznick ("the Niznick Patent") discloses a threaded implant having a lower end which is formed with a hollow, perforated cylindrically-shaped core. A bore is prepared in the jawbone to receive the implant by first forming a hollow cavity having a depth of about one-half the implant's ultimate penetration into the bone. The remainder of the bore is then formed into the jawbone using a special trephine drill which leaves a bone core that mates with the interior of the implant's perforated core. After the implant is screwed into the bore, bone growth or regrowth occurs through the perforations in the implant's core. While the Niznick Patent acknowledges that screw-type dental implants are advantageous because they can immediately support a structural connection, the patent's text expressly states that after the implant installation the gum tissue is to be sutured together over the implant's site for some number of weeks while bone growth or regrowth occurs. Only after this bone growth or regrowth occurs may the implant support a prosthesis. The patent also discloses that engagement between the surrounding bone and the uppermost turn of the implant's external threads blocks infiltration of foreign matter further into the bore. The patent discloses that an implant of this type requires a minimum penetration into the bone of at least 9.5 millimeters.

U.S. Pat. Nos. 5,004,421 and 5,087,199 which respectively issued on Apr. 2, 1991, and on Feb. 11, 1992, based upon an application initially filed on Jul. 27, 1990, by Sargon Lazarof ("the Lazarof Patents"), both disclose an elongated tubular body which fits into a preformed bore in the jawbone. The body includes two sets of internal threads respectively located at each end of the body. Four radial slits are formed along the length of the body at one end which receives a threaded expander. The body also includes external self-taping threads which thread into the bone. To install the implant, the end of the body holding the expander screws into the bore in the jawbone until it bottoms out against the lower surface of the bore. A hexagonal wrench is then inserted into a socket in the expander and the expander is rotated to draw it toward the middle of the body. Movement of the expander toward the middle of the body spreads the portion of the body enclosing the expander outward into the surrounding bone. The body's internal and external threads have opposite handedness so rotation of the expander within the body tends to screw the body deeper into the jawbone rather than out of the jawbone.

Many dental implants being used today, such as that disclosed in the Niznick Patent, do not immediately accept functional loading, e.g. the forces of chewing food. With such implants, as long as six months may elapse between installation of the implant into a patient's jaw and installation of a prosthesis. During this extended interval of time bone regrows around and into an initially loose implant until it to becomes firmly fixed within the jaw. Installing a prosthesis after this long healing period requires a second surgery to expose the head of the implant before attaching the prosthesis. Expanding, screw type dental implants, such as that disclosed in the Flander and Lazarof Patents, attempt to provide an implant that will immediately accept functional loading. Presently, there exist no commercially available dental implants, such as those disclosed in the Ashuckian, Flander and Lazarof Patents, which expand during placement. Furthermore, it appears that the United States Food and Drug Administration ("FDA") has, thus far, not approved any such implants for general use.

Another disadvantage of present commercially available dental implants is that placement at particular locations is inhibited or made more complicated by their excessive length. Placing a long implant in zones having minimal depth of bone, particularly in the posterior maxilla and mandible, can be difficult. In the posterior maxilla, an excessively long implant encroaches on the maxillary sinus. In the posterior mandible, an excessively long implant encroaches on the mandibular neuro-vascular bundle.

One disadvantage of an expanding implant such as those disclosed in the Ashuckian, Flander, and Lazarof Patents is that upon installation they establish a void at the end of the implant deepest within the jaw. Another disadvantage of an expanding implant such as those disclosed both in the Ashuckian, Flander and Lazarof Patents is that they provide passages or openings between the end of the implant deepest within the jaw and the end of the implant which receives a prosthesis. Such passages through the implant may provide an avenue for bacterial infection. Furthermore, it is difficult to collapse an expanding implant such as that disclosed in the Ashuckian and Lazarof Patents immediately or shortly after installation if the implant's removal should become necessary.

SUMMARY OF THE INVENTION

The present invention provides an improved dental implant which may immediately receive a functional loading.

An object of the present invention is to provide a threaded dental implant which may be easily installed.

Another object of the present invention is to provide a dental implant having sufficient stability to permit immediate placement of a fully functional dental prosthesis.

Another object of the present invention is to provide an expandable dental implant which, after installation, has a pre-established, controlled amount of lateral expansion.

Another object of the present invention is to provide a dental implant which facilitates soft tissue healing and adaptation.

Another object of the present invention is to provide a dental implant which permits normal tissue contour around the dental prosthesis immediately after placement.

Another object of the present invention is to provide an expanding dental implant which immediately upon installation does not establish a void within the jaw.

Another object of the present invention is to provide a shorter expanding dental implant which may be readily placed in zones of minimal bone.

Yet another object of the present invention is to provide an expanding dental implant which after installation provides no passage or opening between the end of the implant deepest within the jaw and the top of the implant to which a prosthesis attaches.

Yet another object of the present invention is to provide an implant having stability sufficient to permit cortical, cancellous or corticocancellous bone grafts during concurrent placement of both the implant and the bone graft, particularly in sinus lift procedures, in broadening of the labial/lingual ridge width through veneer grafting, and in neurovascular transposition procedures employing bone grafts.

Yet another object of the present invention is to provide a dental implant which during installation or shortly thereafter may be more easily removed, should removal become necessary.

Briefly, the present invention is an expandable dental implant that is adapted for receiving and supporting a dental prosthesis. The expandable dental implant, which is secured within a bore formed into bone of a patient's jaw, includes an elongated, hollow, tubular barrel having both an attachment end, to which a dental prosthesis may be attached, and an insertion end, which enters furthest into a bore formed into bone of a patient's jaw. The barrel has both an interior surface and an exterior surface which respectively extend from the attachment end of the barrel to its insertion end. The barrel has threads formed both on the interior surface and on the exterior surface of the barrel. The threads formed on the exterior surface of the barrel permit the barrel to be screwed into a bore formed into bone of a patient's jaw. The barrel is pierced about its insertion end by a plurality of radial slits spaced circumferentially around the barrel. The slits pass completely through the barrel from the exterior surface to the interior surface, and extend a distance along the barrel from the insertion end toward the attachment end. The interior surface of the barrel at the insertion end is formed with a smaller diameter than the diameter of the interior surface of the barrel at the attachment end.

The expandable dental implant also includes an expander screw which is inserted into the interior of the barrel through its attachment end. The expander screw is shaped to engage and mate with the threads formed on the interior surface of the barrel. Upon advancement of the expander screw along the barrel from the barrel's attachment end toward its insertion end, an end surface of the expander screw collides with the interior surface of the barrel near its insertion end. Either or both of the colliding surfaces of the expander screw and of the barrel are formed with a shape that generally converges from the attachment end toward the insertion end, such as a frustro-conical shape or an arcuate shape. Consequently, after the barrel has been screwed into a bore formed into bone of a patient's jaw, advancement of the expander screw from the barrel's attachment end toward its insertion end causes the insertion end of the barrel to expand outward into and to penetrate the surrounding bone of a patient's jaw.

The threads on the barrel and on the expander screw are preferably formed so that turning the expander screw within the barrel in a direction which advances the expander screw along the barrel from the attachment end to the insertion end urges the barrel to rotate in a direction which screws the barrel deeper into the bore formed into bone of patient's jaw.

An advantage of the expandable dental implant of the present invention is that; because the threads on the exterior surface of the barrel seal against the bone of a patient's jaw, and because the threads on the expander screw seal against the threads on the interior surface of the barrel; it does not provide any passage or opening between the end of the implant deepest within the jaw and the end of the implant which receives a prosthesis.

Another advantage of the expandable dental implant of the present invention is that advancement of the expander screw from the attachment end toward the insertion end of said barrel causes the expander screw to substantially fill a void resulting from expansion of the insertion end of the barrel into the surrounding bone.

These and other features, objects and advantages will be understood or apparent to those of ordinary skill in the art from the following detailed description of the preferred embodiment as illustrated in the various drawing figures.

BRIEF DESCRIPTION OF THE DRAWINGS

FIG. 1 is a partially sectioned perspective view depicting an expandable implant in accordance with the present invention placed into a bore formed into jaw bone structure before the implant's expansion;

FIG. 2 is a partially sectioned elevational view of a barrel and an elevational view of an expander screw of the implant taken along the line 2—2 in FIG. 1;

FIG. 3 is a partially sectioned elevational view of the expandable implant's insertion end taken along the line 3—3 in FIG. 1 after expansion of the insertion end, in which the generally-converging colliding surfaces both of the expander screw and of the barrel are frustro-conically-shaped;

FIG. 4 is a partially sectioned elevational view of an alternative embodiment of the implant's barrel depicted in FIG. 2; and FIG. 5 is a partially sectioned elevational view, similar to that depicted in FIG. 3, of an alternative embodiment expandable implant's insertion end after expansion of the insertion end, in which the generally-converging colliding surfaces of the expander screw is bullet-shaped and of the barrel is a curved, funnel-shaped.

DETAILED DESCRIPTION OF THE PREFERRED EMBODIMENTS

FIG. 1 depicts an expandable dental implant in accordance with the present invention referred to by the general reference character 10. In the illustration of FIG. 1, the implant 10 has been placed into a bore 12 formed into bone 14 in a patient's jaw. FIG. 1 depicts alveolar bone section 16 having outer cortical bone portion 18 which terminates at the crest 22 where the soft tissue 24 of a patient's jaw meets the outer cortical bone portion 18. The implant 10 includes a unitary, elongated, hollow, tubular barrel 32 having a prosthesis attachment end 34 and an implant insertion end 36. The insertion end 36 of the implant 10 enters furthest into the bore 12, while the attachment end 34 provides a site for attaching a dental prosthesis (Not illustrated in FIG. 1).

Referring now to FIG. 2, the barrel 32 includes an interior surface 42 and an exterior surface 44. Threads 46 are formed on the interior surface 42 of the barrel 32 extending part of the distance from the attachment end 34 to the insertion end 36. Threads 48 are also formed on the exterior surface 44 of the barrel 32 extending part of the distance from the insertion end 36 to the attachment end 34. The threads 48 permit the barrel 32 to be screwed into the bore 12 in the bone 14. The attachment end 34 of the barrel 32 includes a hexagonal head 50 to which a hexagonal socket wrench (Not illustrated in any of the FIGS.) is secured to the barrel 32 by a screw (Not illustrated in any of the FIGS.) while the barrel 32 is being screwed down into the bore 12 in the bone 14. The insertion end 36 of the barrel 32 is pierced by a plurality of slits 52. The slits 52 are spaced circumferentially around the barrel 32, pass completely through the barrel 32 from the exterior surface 44 to the interior surface 42, and extend a distance along the barrel 32 from the insertion end 36 toward the attachment end 34. A circularly-shaped stress relief aperture 54 pierces completely through the barrel 32 from the exterior surface 44 to the interior surface 42 at one end of each slit 52 furthest from the insertion end 36 of the barrel 32. The interior surface 42 of the barrel 32 includes a smaller diameter section 56 at the insertion end 36 than at the attachment end 34. The interior surface 42 of the barrel 32 includes an inverted generally-converging surface 58 at that end of the smaller diameter section 56 nearest the insertion end 36 of the barrel 32. In the embodiment of the implant 10 depicted in FIGS. 2, 3 and 4, the generally-converging surface 58 is formed with an inverted frustro-conical shape.

The implant 10 also includes an expander screw 62 illustrated in FIG. 2. The expander screw 62 includes a hollow socket 64 adapted to receive a hexagonal wrench (Not illustrated in FIG. 2). Threads 66, formed to mate with and engage the threads 46 formed on the interior surface 42 of the barrel 32, surround the socket 64 on an outer surface 68 of the expander screw 62. An end surface 72 of the expander screw 62 furthest from the socket 64 includes a generally-converging surface 74. In the embodiment of the implant 10 depicted in FIGS. 2, 3 and 4, the generally-converging surface 74 is a frustro-conical shape. The outer surface 68 of the expander screw 62 between the threads 66 and the end surface 72 is formed with a smooth, cylindrically shaped surface 76.

As suggested by FIG. 2, the end surface 72 of the expander screw 62 is inserted into the barrel 32 at the attachment end 34 thereof and the threads 66 of the expander screw 62 mate with the threads 46 formed on the interior surface 42 of the barrel 32. Rotation of the expander screw 62 within the barrel 32 in the proper direction advances the expander screw 62 along the barrel 32 from the attachment end 34 toward the insertion end 36. The threads 46 formed on the interior surface 42 of the barrel 32 and the threads 48 formed on the exterior surface 44 thereof are preferably arranged such that turning the expander screw 62 within the barrel 32 in a direction which advances the expander screw 62 toward the insertion end 36 urges the barrel 32 to rotate in a direction which screws the barrel 32 deeper into the bore 12 formed into the bone 14 of a patient's jaw. After the barrel 32 has been screwed into a bore 12 formed in the bone 14, the expander screw 62 is rotated within the barrel 32 to advance the expander screw 62 toward the insertion end 36 until the generally-converging surface 74 of the end surface 72 collides with the generally-converging surface 58 of the interior surface 42.

Referring now to FIG. 3, further rotation of the expander screw 62 to advance the expander screw 62 toward the insertion end 36 causes the insertion end 36 of the barrel 32 to expand outward into and to penetrate the bone 14 surrounding the implant 10. Expansion of the insertion end 36 continues as the expander screw 62 continues advancing toward the insertion end 36 until the generally-converging surface 74 of the end surface 72 passes beyond the generally-converging surface 58 of the interior surface 42, and the generally-converging surface 58 slides along the cylindrically shaped surface 76 of the outer surface 68. After the generally-converging surface 58 begins sliding along the cylindrically shaped surface 76, the insertion end 36 expands no further into the surrounding bone 14 even though the expander screw 62 continues advancing toward the insertion end 36 of the barrel 32 until it can be advanced no further. Accordingly, the respective shapes of the cylindrically shaped surface 76 of the expander screw 62 and the interior surface 42 of the barrel 32 pre-establish a maximum amount by which the insertion end 36 of the barrel 32 may be expanded outward into the bone 14.

After the implant 10 has been secured in the bone 14 of a patient's jaw, a two-piece dental prosthesis is attached to the implant 10 by a threaded pillar (Not illustrated in any of the FIGS.) which screws into and mates with the threads 46 formed on the interior surface 42 of the barrel 32. A portion of the prosthesis immediately adjacent to the attachment end 34 of the barrel 32 is a washer-like cap (Not illustrated in any of the FIGS.) which fits over and envelopes the hexagonal head 50 at the attachment end 34 of the barrel 32 to create a smooth outer surface for the combined implant 10 and prosthesis. The distal portion of the prosthesis may be a single tooth, an abutment for a multi-tooth bridge, a support for an overdenture superstructure, a support for a fixed or detachable prosthesis, and in some instances an anchorage for an orthodontic retraction mechanism.

The barrel 32 and the expander screw 62 are preferably made from 95% pure titanium alloy. The threads 48 on the exterior surface 44 of the barrel 32 are preferably a 3.75 mm diameter metric thread, and the unthreaded portion of the exterior surface 44 preferably has a diameter $D_B$ of 3.75 mm. The barrel 32 may be fabricated to have various different standard lengths $L_B$, such as 16 mm, 14 mm, 12 mm, 10 mm and 8 mm, from the insertion end 36 of the barrel 32 to the attachment end 34 thereof. The expander screw 62 used with a barrel 32 having a specified length $L_B$ preferably has a length $L_s$ which is 2.8 mm shorter than the length $L_B$ of the barrel 32. A 2.5 diameter metric thread is preferably used for the threads 46 and 66 formed respectively on the interior surface 42 of the barrel 32 and on the outer surface 68 of the expander screw 62. The included angle for the frustro-conically-shaped generally-converging surfaces 58 and 74 is preferably 30°. The shapes respectively of the smaller diameter section 56 of the interior surface 42 of the barrel 32 and the outer surface 68 of the expander screw 62 are preferably formed so the insertion end 36 of the barrel 32 expands 2.0 mm when the expander screw 62 advances as far as permitted toward the insertion end 36 of the barrel 32. There preferably are four slits 52 space uniformly about the circumference of the insertion end 36 of the barrel 32. However, for a barrel 32 having a length less than 10 mm, six slits 52 may be uniformly spaced about the circumference of the insertion end 36.

Referring now to FIG. 4, that FIG. depicts an alternative embodiment of the barrel 32. Those elements depicted in FIG. 4 that are common to the barrel 32 depicted in FIG. 2 carry the same reference numeral distinguished by a prime ("'") designation. For a barrel 32' having a length $L_B$ less than 10 mm, an oval-shaped stress relief aperture 82 may pierce completely through the barrel 32 from the exterior surface 44 to the interior surface 42 rather than the circularly-shaped stress relief aperture 54 depicted in FIGS. 1, 2 and 3. Barrels 32 having a length $L_B$ of 8 mm are particularly useful for implantation in locations having minimal depth of bone. Thus, such a short implant 10 is particularly useful in placing a dental prosthesis in the posterior maxilla and mandible.

FIG. 5 depicts an alternative embodiment for the generally-converging surfaces 58 and 74 respectively of the barrel 32 and of the expander screw 62. Those elements depicted in FIG. 5 that are the same as the elements depicted in FIG. 3 bear the same reference numeral distinguished by a double prime ("''") designation. In the embodiment of the implant 10 depicted in FIG. 5, the generally-converging portion of the end surface 72" of the expanding screw 62" is formed with a bullet-shaped arcuate surface 94, and the generally-converging portion of the interior surface 42" of the barrel 32" is formed with a curved, funnel-shaped arcuate surface 96.

Although the present invention has been described in terms of the presently preferred embodiment, it is to be understood that such disclosure is purely illustrative and is not to be interpreted as limiting. For example, both colliding surfaces 42 and 72 respectively of the barrel 32 and of the expander screw 62 need not necessarily be formed with a generally-converging shape. Only the colliding surface 42 of the barrel 32 or the colliding surface 72 of the expander screw 62 need include the generally-converging surface. If only the interior surface 42 of the barrel 32 or only the end surface 72 of the expander screw 62 is formed with a generally-converging shape, then the collision of the two surfaces 42 and 72 causes that surface which is not formed with a generally-converging shape to slide along the opposing generally-converging surface while concurrently deforming to some extent depending upon the force present during the collision between the two surfaces 42 and 72. An implant 10 in accordance with the present invention may include colliding surfaces 42 and 72 having shapes other than frustro-conical or arcuate. The present invention requires only that colliding surfaces 42 and 72 generally-converge from the attachment end 34 of the barrel 32 toward the insertion end 36 thereof. When such generally-converging colliding surfaces 42 and 72 hit each other the colliding surfaces 42 and 72 slide past each other while concurrently causing the insertion end 36 of the barrel 32 to expand outward into and to penetrate the bone 14 surrounding the implant 10. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. An expandable dental implant which may be secured within a bore formed into bone of a patient's jaw that is adapted for receiving and supporting a dental prosthesis, said expandable dental implant comprising:

an elongated, hollow, tubular barrel having both an attachment end, to which a dental prosthesis may be attached, and an insertion end, which enters furthest into a bore formed into bone of a patient's jaw; said barrel having both an interior surface and an exterior surface which respectively extend from the attachment end of said barrel to the insertion end; said barrel having threads formed both on the interior surface and on the exterior surface of said barrel; the threads formed on the exterior surface of said barrel permitting said barrel to be screwed into a bore formed into bone of a patient's jaw; said barrel being pierced about the insertion end thereof by a plurality of radial slits spaced circumferentially around said barrel; the slits passing completely through said barrel from the exterior surface to the interior surface, and extending a distance along said barrel from the insertion end toward the attachment end; the interior surface of said barrel at the insertion end having a smaller diameter than that of the interior surface of said barrel at the attachment end; and an expander screw adapted for insertion into said barrel through the attachment end thereof; said expander screw having an outer surface that is shaped to engage and mate with the threads formed on the interior surface of said barrel; said expander screw having an end surface, which upon advancement of said expander screw along said barrel from the attachment end toward the insertion end thereof, collides with the interior surface of said barrel near the insertion end thereof; the end surface of said expander screw and the interior surface of said barrel near the insertion end thereof each constituting a colliding surface respectively of said expander screw and of said barrel; one of the colliding surfaces of said mated expander screw and barrel being formed with a shape that generally-converges from the attachment end of said barrel toward the insertion end thereof; whereby, after said barrel has been screwed into a bore formed into bone of a patient's jaw, advancement of the expander screw from the attachment end toward the insertion end of said barrel causes the insertion end of said barrel to expand outward into and to penetrate the surrounding bone, and causes the expander screw to substantially fill a void resulting from expansion of the insertion end of the barrel into the surrounding bone.

2. The expandable dental implant of claim 1 wherein the generally-converging colliding surface either of said expander screw or of said barrel is formed with a frustroconical shape.

3. The expandable dental implant of claim 1 wherein the generally-converging colliding surface either of said expander screw or of said barrel is formed with an arcuate shape.

4. The expandable dental implant of claim 1 wherein the colliding surfaces both of said expander screw and of said barrel are respectively formed with generally-converging shapes.

5. The expandable dental implant of claim 4 wherein the generally-converging colliding surfaces both of said expander screw and of said barrel are respectively formed with frustro-conical shapes.

6. The expandable dental implant of claim 4 wherein the generally-converging colliding surfaces both of said expander screw and of said barrel are respectively formed with arcuate shapes.

7. The expandable dental implant of claim 4 wherein one of the generally-converging colliding surfaces either of said expander screw or of said barrel is formed with a frustroconical shape and the other generally-converging colliding surface is formed with an arcuate shape.

8. The expandable dental implant of claim 1 wherein a circularly-shaped aperture pierces completely through said barrel from the exterior surface to the interior surface thereof at an end of each slit furthest from the insertion end of said barrel.

9. The expandable dental implant of claim 1 wherein an oval-shaped aperture pierces completely through said barrel from the exterior surface to the interior surface thereof at an end of each slit furthest from the insertion end of said barrel.

10. The expandable dental implant of claim 1 wherein of the threads formed on the interior surface and on the exterior surface of said barrel are arranged such that turning the expander screw within the barrel in a direction which advances the expander screw along the barrel from the attachment end to the insertion end urges said barrel to rotate in a direction which screws said barrel deeper into the bore formed into bone of patient's jaw.

11. The expandable dental implant of claim 1 wherein the outer surface of said expander screw and the interior surface of said barrel are shaped such that continued advancement of the expander screw toward the insertion end of the barrel causes only a pre-established expansion of the insertion end outward into the bone surrounding the barrel.

12. The expandable dental implant of claim 1 wherein said barrel has a length $L_B$ from the insertion end of said barrel to the attachment end of said barrel that is less than 10 mm.

13. A method for placing an expandable dental implant, that is adapted to receive and support a dental prosthesis, into a bore formed into bone of a patient's jaw, the method comprising:

preparing a bore for receiving an expandable dental implant in bone of a patient's jaw;

screwing an elongated, hollow, tubular barrel into the bore; the barrel having both an attachment end, to which a dental prosthesis may be attached, and an insertion end, which enters furthest into the bore; the barrel having both an interior surface and an exterior surface which respectively extend from the attachment end of the barrel to the insertion end; the barrel having threads formed both on the interior surface and on the exterior surface of the barrel; the threads formed on the exterior surface of the barrel permitting the barrel to be screwed into a bore formed into bone of a patient's jaw; the barrel being pierced about the insertion end thereof by a plurality of radial slits spaced circumferentially around the barrel; the slits passing completely through the barrel from the exterior surface to the interior surface, and extending a distance along the barrel from the insertion end toward the attachment end; the interior surface of the barrel at the insertion end having a smaller diameter than that of the interior surface of the barrel at the attachment end; and rotating an expander screw to advance the expander screw along the barrel from the attachment end toward the insertion end thereof; the expander screw being adapted for insertion into the interior of the barrel through the attachment end of the barrel; the expander screw being shaped to engage and mate with the threads formed on the interior surface of the barrel; the expander screw having an end surface, which upon advancement of the expander screw toward the insertion end collides with the interior surface of the barrel near the insertion end thereof; the end surface of said expander screw and the interior surface of said barrel near the insertion end thereof each constituting a colliding surface respectively of said expander screw and of said barrel; one of the colliding surfaces being formed with a shape that generally-converges from the attachment end of said barrel toward the insertion end thereof; whereby advancement of the expander screw from the attachment end toward the insertion end of the barrel causes the insertion end of the barrel to expand outward into and to penetrate the surrounding bone.

14. The method of claim 13 wherein turning the expander screw within the barrel in a direction which advances the expander screw along the barrel from the attachment end to the insertion end urges the barrel to rotate in a direction which screws the barrel deeper into the bore formed into bone of patient's jaw.

15. The method of claim 13 further comprising the step of attaching a dental prosthesis to the attachment end of the barrel.

* * * * *